(12) United States Patent
Piper

(10) Patent No.: US 6,299,886 B1
(45) Date of Patent: Oct. 9, 2001

(54) MINERAL AND VITAMIN COMBINATIONS FOR THE TREATMENT OF STRESS AND ALLERGIES

(76) Inventor: Edwina M Piper, Balgowan Cottages, By Leven, Fife (GB), KY8 5NJ ( * ) Notice: Subject to any disclaimer, the term of this patent is extended or adjusted under 35 U.S.C. 154(b) by 0 days.

(21) Appl. No.: 09/462,990

(22) PCT Filed: Jul. 17, 1998

(86) PCT No.: PCT/GB98/02128

§ 371 Date: Apr. 25, 2000

§ 102(e) Date: Apr. 25, 2000

(87) PCT Pub. No.: WO99/03482

PCT Pub. Date: Jan. 28, 1999

(30) Foreign Application Priority Data

Jul. 19, 1997 (GB) ................................................. 9715203

(51) Int. Cl.⁷ ........................................................ A61K 9/00
(52) U.S. Cl. .................... 424/400; 424/45; 424/195.1; 424/464; 424/692; 514/826; 514/861; 514/863; 514/474
(58) Field of Search .................................... 424/400, 464, 424/195.1, 45, 692; 514/826, 861, 863, 474

(56) References Cited

U.S. PATENT DOCUMENTS

| | | | |
|---|---|---|---|
| 5,270,297 | * 12/1993 | Paul et al. | 514/23 |
| 5,597,585 | 1/1997 | Williams et al. | 424/579 |
| 6,139,872 | * 10/2000 | Walsh | 424/466 |

FOREIGN PATENT DOCUMENTS

WO 97 26897    7/1997   (WO) .

OTHER PUBLICATIONS

Database WPI Section Ch, Week 9335 Derwent Publications Ltd., London, GB; AN 93–273270 XP002082115 & CA 2 057 463 A (Creative Nutrition Canada Corp), Jun. 12, 1993 see abstract.

* cited by examiner

Primary Examiner—Thurman K. Page
Assistant Examiner—Lakshmi Channavajjala
(74) Attorney, Agent, or Firm—Nixon & Vanderhye

(57) ABSTRACT

The treatment is by means of nutritional supplements for the adrenal glands, liver and mast cells. The supplements may include potassium, magnesium, Vit $B_6$, Vit $B_5$, Vit C and EFA. A biological mechanism linking stress and allergies such as hayfever or other perennial or seasonal respiratory allergies is proposed and the effect of the treatment thereon is discussed.

8 Claims, 3 Drawing Sheets

---

STRESS ACTIVATES ADRENAL GLANDS WHICH RAPIDLY DEPLETES VITAMIN & MINERAL STOCKS. REPROVISIONS FROM THE LIVER & OTHER ORGANS, BLOODSTREAM AND TISSUES.

STRESS DEPLETES LIVER NUTRIENT LEVELS FOR NORMAL DETOXIFICATION PROCESS AND IMMUNE RESPONSE.
UNABLE TO SUPPLY ADEQUATE PHOSPHOLIPIDS AND HISTAMINASE.

MAST CELL AFFECTED
INCREASED PERMEABILITY AND INTERCELLULAR DISRUPTION
−MAST CELL FAILURE
−ALLERGIC REACTION

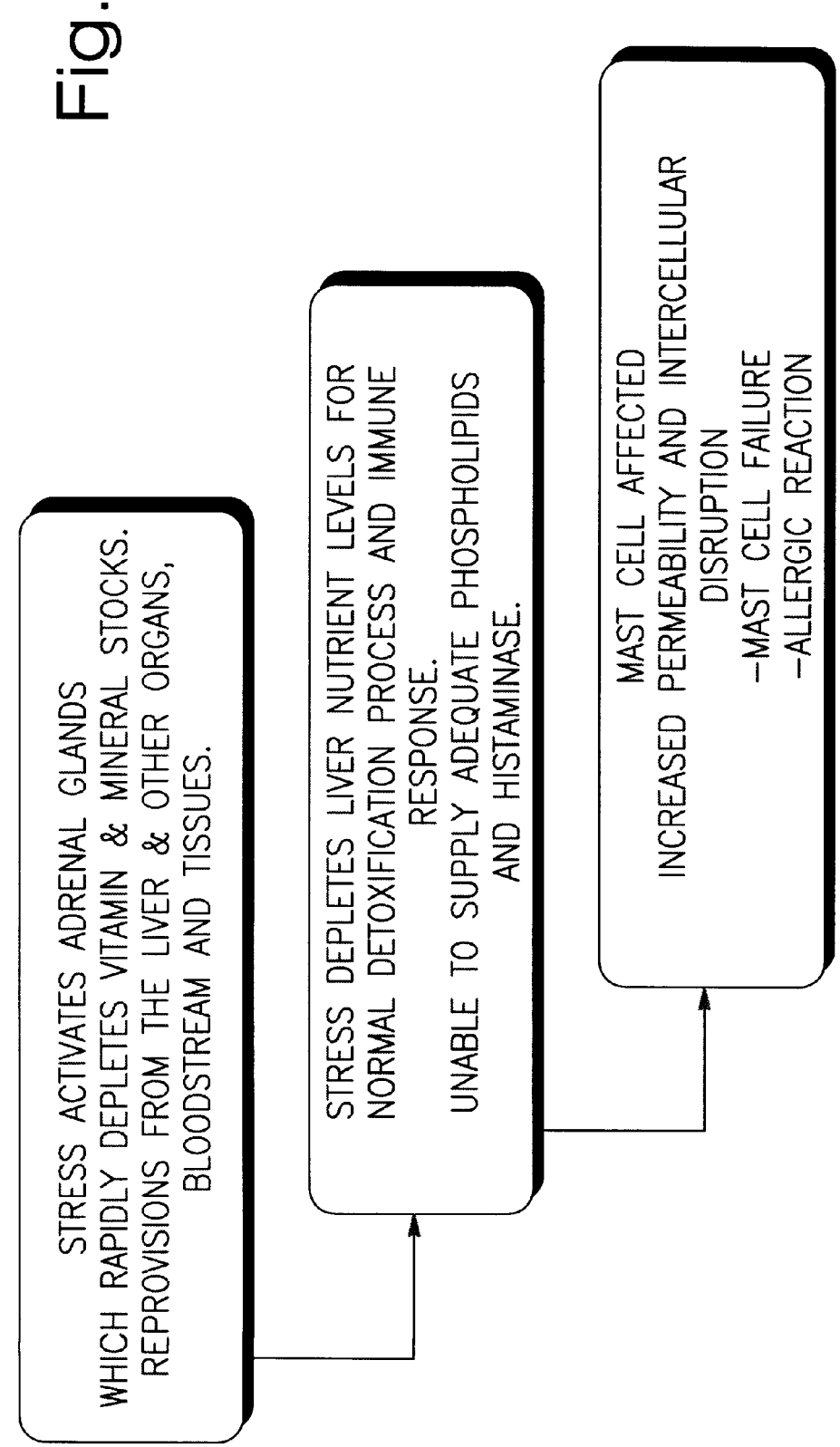

MINERAL AND VITAMIN COMBINATIONS FOR THE TREATMENT OF STRESS AND ALLERGIES

This application is a 371 of PCT/AB98/02128, filed Jul. 7, 1998.

FIELD OF THE INVENTION

This invention relates to novel treatments for allergies such as hayfever and other seasonal and perennial respiratory allergies which the inventor believes are triggered by stress.

THE INVENTION

The invention is set out in the claims herein but simply stated the inventor has devised a method of treating stress and/or allergies, such as hayfever and other seasonal or perennial respiratory allergies, by the co-administration, either simultaneously or sequentially, of ingredients comprising potassium, magnesium, Vit $B_6$, Vit $B_5$, Vit C and an n-6 or n-3 essential fatty acid (EFA) particularly GLA or DGLA. These ingredients (hereinafter "active ingredients") alone are effective but optionally may be combined with other synergistic nutrients.

The invention also extends to compositions comprising those active ingredients in unit dosage form, effective in the treatment of those conditions, and the use of those active ingredients in the manufacture of a medicament, as a single composition or as sub-compositions for co-administration, for treatment of those conditions. The method composition and use of the invention may be applied to the treatment of a human or non-human (preferably mammalian) animal body.

The active ingredients may be present in combination with any pharmaceutically acceptable carrier and may be in any assimilable form for any particular ingredient as well known to those skilled in the art.

In one embodiment the composition comprises the active ingredients in capsule or other form in amounts as follows, and was administered in daily doses:

| | |
|---|---|
| Potassium Gluconate | 10 mg to 5000 mg preferably 100 mg to 1000 mg and very preferably 100 mg to 400 mg. |
| Magnesium Oxide | 1.0 mg to 1000 mg preferably 10 mg to 500 mg and very preferably 50 mg to 300 mg. |
| Pyridoxine Hydrochloride (Vit $B_6$) | 0.1 mg to 500 mg preferably 5 mg to 200 mg and very preferably 10 mg to 100 mg. |
| Pantothenic Acid (Vit $B_5$) | 0.1 mg to 1000 mg preferably 10 mg to 500 mg and very preferably 50 mg to 300 mg. |
| Ascorbic Acid (Vit C) | 10 mg to 5000 mg preferably 100 mg to 2000 mg and very preferably 500 mg to 1000 mg. |
| GLA, for example from Evening Primrose Borage or Blackcurrant | 10 mg to 5000 mg preferably 100 mg to 2000 mg and very preferably 400 mg to 1000 mg. |

The following are synergistically supporting ingredients which optionally may be included in the formula:
Fish Oils to supply n-3 EFAs; Vitamins selected from Vit $B_1$ Thiamine; Vit $B_2$ Riboflavin; Folic Acid; Vit $B_{12}$ Cyanocobalamin; Vit $B_3$ Niacinamide; Vit A Beta Carotene; Vit D Ergocalciferol; Vit E; Biotin; Bioflavonoids; Choline; Inositol; and minerals and trace elements selected from bioavailable forms of Boron; Phosphorus; Manganese; Sodium; Copper; Iron; Zinc; Calcium; Selenium.

The composition may provide the six primary active ingredients alone or may provide these together with one or more of the listed optional minerals and other materials important in the stress response. Vit E may optionally be given in a daily dose of 1 mg to 600 mg, preferably 10 mg to 400 mg and very preferably 10 mg to 50 mg.

The compositions according to the invention may be administered in any convenient form known to those skilled in the art. These forms include capsules of various types, powders, tablets, solutions, suspensions, emulsions and aerosol sprays. The composition may be administered orally, enterally, parenterally or transdermally using appropriate technology known to those skilled in the art. For complete and effective control of allergic symptoms, the composition is intended for administration on a daily basis.

Further preferred features of the invention are in the dependent claims. An illustrative treatment regimen embodying the invention and what is believed to be a possible underlying physiological mechanism are described below with reference to the drawings in which:

FIG. 1 is a simplified flow diagram showing the interaction of adrenal stress response with the liver and mast cells;

EXAMPLE

Figure 2A:
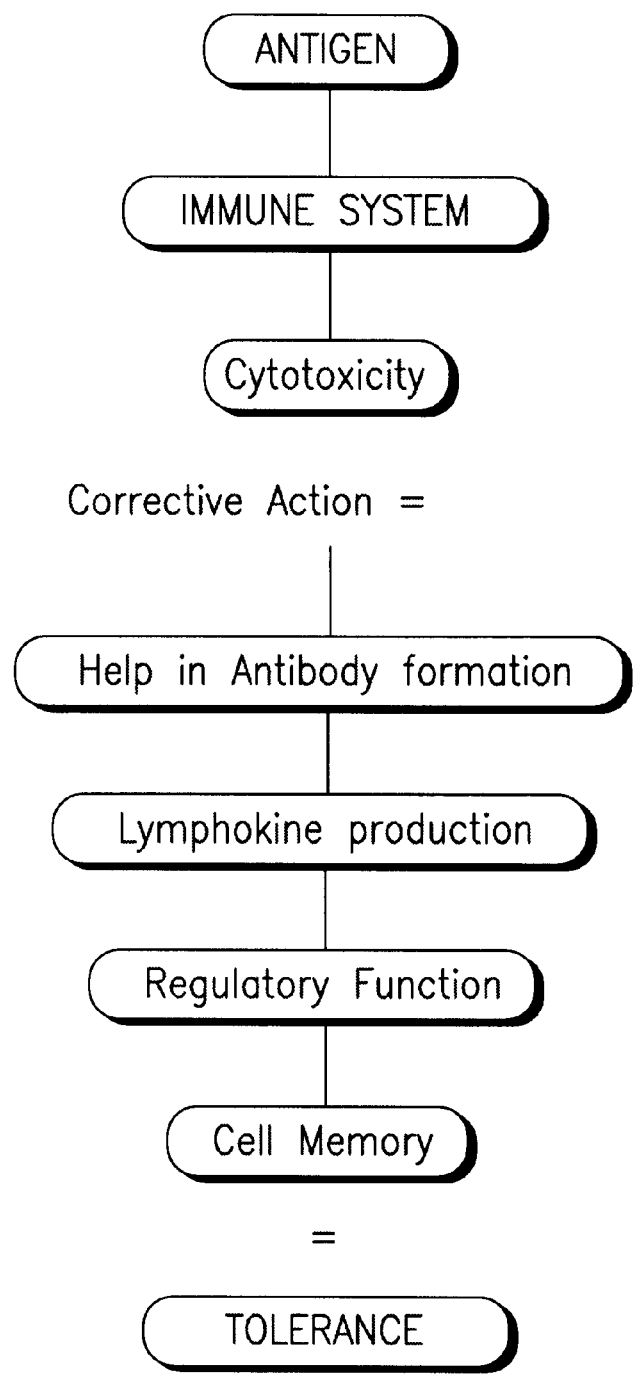
FIG. 2(a) shows the normal antigen response at cellular level.

The following formula was administered to volunteers and after 4 days of ingestion was completely successful in eliminating all allergic symptoms:

| | |
|---|---|
| Potassium as gluconate | 408 mg |
| Evening Primrose Oil (10% GLA) | 500 mg |
| Vit C | 530 mg |
| Bioflavonoids | 25 mg |
| Magnesium as oxide | 134 mg |
| Vit $B_6$ Pyridoxine | 50 mg |
| Vit $B_5$ (d-pantothenic acid) | 50 mg |
| Vit $B_1$ (thiamine) | 5 mg |
| Vit $B_2$ (riboflavin) | 5 mg |
| Bioavailable Zinc | 8 mg |
| Bioavailable Manganese | 2 mg |
| Bioavailable Selenium | 25 μg |
| Bioavailable Chromium | 25 μg |

Withdrawal of treatment led to a return of symptoms within an average of seven days.

The following considers the allergic response to toxic stress, induced by an abnormal biochemical response to antigens and elucidates a therapeutic nutritional approach, designed to counteract the biochemical effects of toxic stress. Whether or not the theory on which the formulation is based is correct, the inventor has found this approach to be effective in treating respiratory allergy and its full range of symptoms.

Proposition

Allergies such as perennial and seasonal respiratory allergies may be caused by nutritional deficiency precipitated by toxic stress, resulting in an impaired immune response which reacts abnormally to innocuous antigens. Compositions and methods of treatment according to the invention are designed to supplement nutrient levels to combat stress in three active sites: the adrenal glands, liver and mast cells.

Stress

Stress which applies any sort of biological pressure upon the body has a number of origins e.g. chemical pollution, emotional, hormonal, viral and bacterial disease. Social pressures upon individuals, present levels of pollution (i.e. airborne, chemicals in agriculture and food manufacture, industry, internal combustion engines), plus naturally occurring toxins in the metabolism invoke a stress reaction. This in turn can trigger a number of physical disorders including an autoimmune reaction where the thyroid, adrenal cortex and joints are often affected. Also an individual may become prone to allergies.

The Biochemical Stress Reaction

Stress causes a biochemical reaction which is both toxic and disruptive to the metabolism. Biochemical stress of any sort provokes adrenal gland activity (FIG. 1). The adrenal glands require sugar energy to combat stress. This is obtained by cytolysis and proteins are destroyed. Initially sacrificial proteins in the thymus and lymph glands are utilised; thereafter sugar is obtained by a general invasion of any available proteins. The by-product of this ongoing cell death is histamine, which the liver neutralises with histaminase.

Frequent or prolonged stress, at any level of severity, prompts the adrenal glands to take defensive action and makes heavy demands upon available nutrients, which they provision from the bloodstream, bones, soft tissues and major organs, including the liver. An important function of the liver is the de-toxification of the bloodstream. It is also a major factor in the immune system. Sustained adrenal stress creates demands upon the liver, which sets up a degrading nutrient spiral, as liver nutrients are acquisitioned by the adrenal activity and also expended in the detoxification process. In this 'stage of resistance' to stress, if all available nutrients are expended, and insufficient nutrients provisioned by diet, the adrenal glands can become exhausted and the liver can be damaged. With insufficient nutrient availability, the adrenal glands cease to function, the liver is unable to regenerate itself or maintain its vital functions, the immune system is impaired, important biochemical processes are impeded and the body is rendered susceptible to disease.

Stress And Respiratory Allergy

The Mast Cell

The mast cell is situated in the skin and mucous membranes. It is the body's first defence against external antigens. Its function is to trap and then assist in the destruction of invading organisms and foreign proteins which could harm the biochemistry of the body. FIG. 2a is a simplified illustration of the sequence of responses to antigens at cellular level in a non-allergic state. In order to defend itself, the mast cell has a double membrane heavily fortified by phospholipids (supplied by the liver). This double membrane becomes permeable and subject to invasion by foreign proteins, if not liberally supplied with nutrients, including these phospholipids.

Intracellular Environment

The intracellular pH and composition of the mast cell is under the control of potassium. Potassium is needed by the adrenal glands in large quantity during the stress resistance stage and is utilised in glycolysis to provide sugar energy. The adrenals also require supplies of lipids. As mast cells exist in abundance, they may be an easily obtainable source of potassium and lipids for the adrenal gland stress response. It is notable that the potassium and lipid content of the mast cell is crucial to its function and survival and depletion will have a profound impact.

Sodium and Potassium

Potassium largely resides intracellularly, while sodium is normally present extracellularly. These two cations exist in roughly equal proportion. Sodium and potassium are antagonistic towards each other and an abundance of one will drive out the other.

Membrane Permeability

The mast cell membrane will become 'brittle' and rendered markedly more permeable by insufficient phospholipids. This allows sodium and calcium to be transported across the bi-membrane and into the intracellular environment, driving out potassium and magnesium, which is the first stage in the allergic cascade. Cell disruption results for the following reasons:

a. With few exceptions, most enzymes cannot tolerate sodium. Therefore, within the mast cell, normal enzymatic activity is impeded.

b. Intracellular potassium is responsible for carbohydrate and protein metabolism and enzymatic reactions including the hydrolysis of ATP, which actively controls the transport of ions across the cell membrane.

When potassium is displaced by sodium, all of these biochemical processes are disrupted. Aldosterone, produced by the adrenal glands in the stress reaction is responsible for the retention of sodium and water which drives out potassium. Therefore, confronted with antigen, under adrenal stress conditions, a sensitised mast cell may be already rendered susceptible to intracellular invasion because of:

(a) adrenal stress nutrient demands (including intracellular potassium and membrane lipids)

(b) sodium displacement of potassium, as a result of aldosterone activity.

Either of these events will have a profound effect. As intracellular potassium is removed/expelled, sodium, water and calcium enter to replace it. This results in acute cellular oedema which effects a pH alteration. The cell structure, including the bi-membrane, alters in shape and cytoskeletal organisation. This process is reversible via the sodium pump and if the cell's oxygen supply is brought back to normal.

Figure 2B:
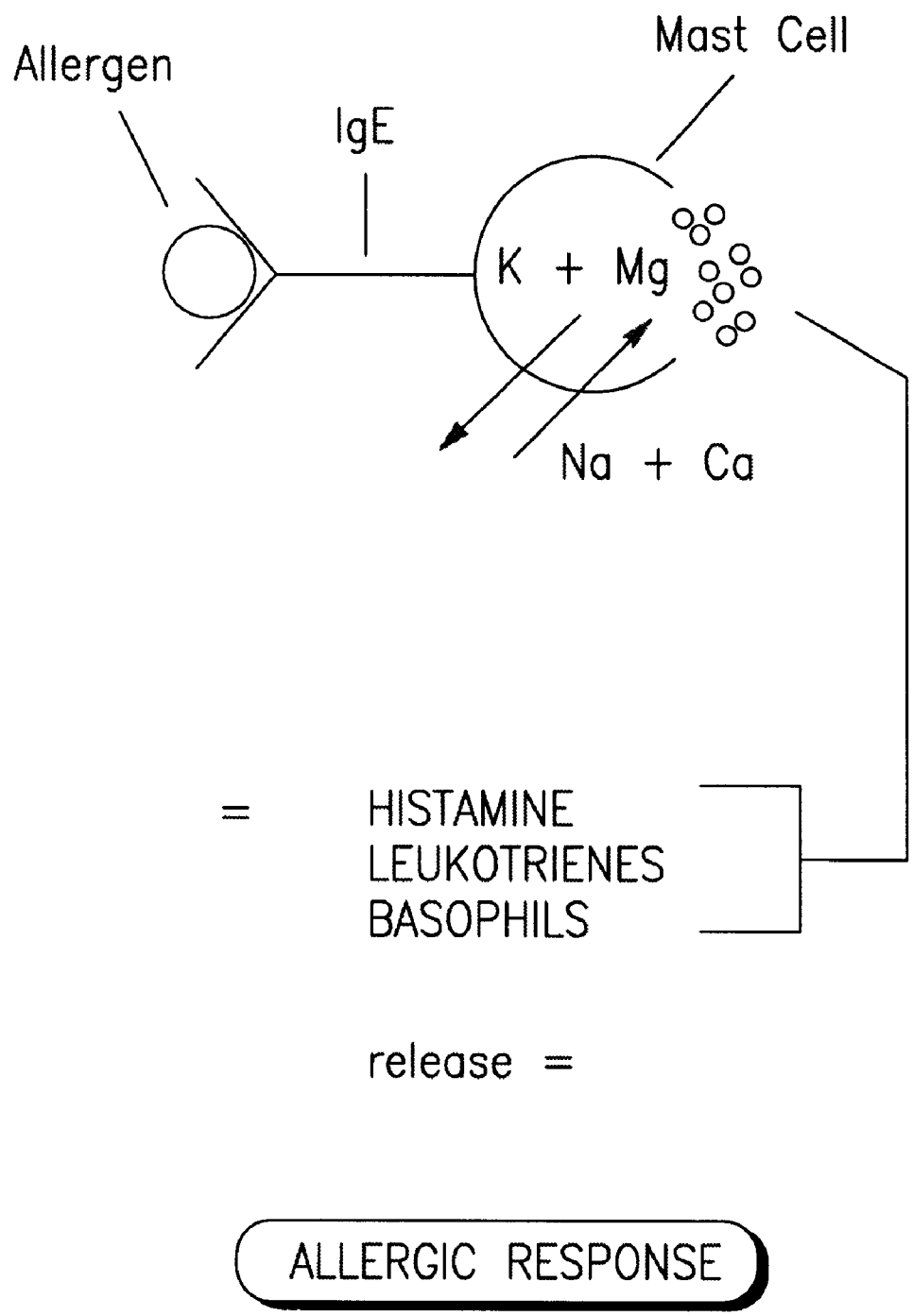
FIG. 2(b) shows the allergic response at sensitised mast cell level.

It seems probable that activity of the antigen/IgE coupling, under these conditions, would find the mast cell vulnerable and completely unable to defend itself. Furthermore, the cellular oedema may lower pH to a level which is exactly suitable for the histidine/histamine conversion. And if the enzyme histidine carboxylase, which converts histidine to histamine, happens to be one of the few enzymes unaffected by sodium, this may cause the mast cell to enter a state of irreversible cytotoxicity, degranulate and release its own toxins, primarily histamine, which result in the allergic reaction. Therefore allergic respiratory disease is perhaps the end result of a biochemical chain reaction within the body, in which the mast cell is attacked on two levels, endogenously by the stress reaction and externally by antigen. (FIG. 2b).

The Allergic Reaction

Traditionally, antihistamine medicaments have formed the basis of medical therapy. These medicaments aim to treat the symptoms of the acute stage of allergic reaction, by blocking the release of histamine in an attempt to circumvent the allergic cascade, but do not aspire to eradicate the disease. The inventor's approach is founded upon nutritional supplementation, which aims to satisfy stress derived nutrient demands and reinforce the body's immune system; thereby allowing this defensive biochemistry to deal with antigens efficiently, as it naturally does in non-allergic individuals. However, it has been found that such reinforcement takes time to reach optimum effect. Typically, a daily ingestion of a composition embodying the invention for 3–4 days is necessary, whereafter all allergic reaction symptoms cease.

The medically accepted cause of an allergic reaction may be defined as follows:

An allergic reaction occurs due to the excessive immune response to some non-threatening foreign protein, initiated when IgE bearing B cells are activated by antigen to secrete IgE antibody. These bind mast cells and basophils resulting in degranulation and release of histamine and other potent mediators causing allergic symptoms such as long term inflammatory effects. Allergic symptoms result from the overwhelming release of histamine and other mediators into the biochemistry of the body.

In answer to the question why some individuals become allergic when others do not, it is suggested here that the mast cell's intrinsic nutritional state of readiness to deal with antigen is a major contributor in resistance to antigen, or conversely in initiation of the allergic cascade. It is further suggested that the nutritional state of the adrenal glands and the liver will mediate the degree of severity of the allergic cascade at mast cell level. The liver supplies vital nutrients to both adrenals and mast cells and detoxifies the bloodstream. The sacrificial mast cell is the first line of defence against invasion of antigens. It may also be first in line as a readily available source of lipids and potassium. Any disruption of adrenal or liver function will affect the mast cell's nutrient status and defensive capability. The biochemical response to the effect of allergen invasion at each of these sites will be governed by their nutritive state. If well supplied with the essential nutrients, these three sites, in concert, will neutralise the allergen and its toxic potential and establish a state of tolerance. A healthy adrenal system will produce adequate cortisone. A healthy liver will support the immune system and produce adequate histaminase to neutralise any histamine produced in reaction to the stress. A healthy mast cell has sufficient phospholipids (supplied by the liver) to maintain correct permeability of its membrane in order to defend itself from abnormal biochemical alteration. This alteration may be the result of penetration by the allergen/IgE chemotactic signal or the adrenal stress effects upon its biochemistry.

The methods and composition of the invention are intended to supplement nutrient requirements and hence may:

(a) reduce mast cell membrane permeability, (b) supply appropriate nutrients to encourage 'normal tolerance' to antigen.

(c) maintain favourable pH levels in the mast cell.

(d) supply sufficient nutrients to the adrenal glands in order to serve the stress reaction, including potassium for glycolysis.

(e) supply the liver with nutrients to maintain adequate function to serve the immune system.

By addressing the nutrient requirements of the adrenal glands, the formula minimises the burden of nutritional provision by the liver, thus allowing this organ to continue to utilise its stocks in support of the immune system (including the mast cell), thereby enhancing immunity and assisting in establishing 'normal tolerance to antigen' in the mast cell. As demonstrated in strictly confidential tests upon volunteers, this approach appears wholly effective in completely eliminating all symptoms of allergic respiratory conditions. The composition is equally effective in seasonal and perennial forms of this condition. Further, it has been noted that allergic individuals sense of smell and taste was also restored, even after years of sensory impairment. Also, subjects taking the composition on a daily basis have entered highly allergenic environments with no ill effects whatsoever. Even those with extremely long term perennial allergies (i.e. 20 years plus) are able to come into contact with known allergens without suffering any allergic reaction.

While it is accepted that the foregoing hypothesis must be independently tested and clinically proven, it is the suggestion of the inventor that the biochemical consequences of stress may be a primal cause in allergic reactions. The success of the composition in completely eliminating all symptoms of allergic reaction in sensitive individuals, may demonstrate that it is not inevitable that an allergen sensitised mast cell is constrained to enter the cytototoxicity/degranulation/histamine release cycle.

The composition is designed to address substantially the whole process of the allergic reaction, cause and effect, within the major sites involved, i.e. adrenal glands, liver and mast cell in the case of hayfever. An appropriately modified balance of the active ingredients may be effective in treating other allergic conditions, some of which are allergic asthma, urticaria, hives, eczema, psoriasis and allergic conjunctivitis. For instance, in the case of eczema and psoriasis, it would be expected to increase the percentage of EFA, Vit C, Vit $B_6$ and the minerals magnesium and zinc, with respect to the example given above, which is formulated primarily for the treatment of hayfever and Vit E will specifically be added. With allergic asthma, it may be appropriate to increase Vit $B_6$, Vit C and magnesium.

The composition and treatment method has also been tested on horses suffering from chronic obstructive pulmonary disease ("stable cough": an allergy to dust and moulds found in hay), laminitis ("founder": an allergy to histamines in grass) and allergic eczema("sweet itch": an allergic reaction to biting insects). Doses were calculated according to body weight and administered daily. In all cases symptoms were reduced and controlled within four days and eradicated within seven days. This would suggest that organic allergic reactions in all mammalian bodies may respond favourably to the composition and treatment method.

Furthermore, as this therapeutic nutritional approach is predicated upon counteracting the biochemical effects of toxic stress, the model offered may be applicable to the management of all stress related diseases. Although it is not suggested here that the composition is a complete nutritional supplement, it is suggested that a suitably modified formulation of the stated ingredients would be an appropriate daily nutritional supplement to be taken prophylactically against all forms of existing and anticipated stress. It is further suggested that the composition may be beneficial if taken concurrently with medicaments prescribed for symptom control of stress induced diseases, such as arthritis and essential hypertension (not caused by atherosclerosis or renal failure), with the expectation that the composition would biochemically ameliorate the stress effect, which underlies the disease. This, in turn, may effect a reduction cessation of symptoms.

What is claimed is:

1. A method of treating an allergy comprising administering a composition comprising potassium gluconate, magnesium oxide, pyridoxine hydrochloride, pantothenic acid, ascorbic acid and an n-3 or n-6 essential fatty acid.

2. A method of treating hay fever or other seasonal or perennial allergy comprising administering a composition comprising potassium gluconate, magnesium oxide, pyridoxine hydrochloride, pantothenic acid, ascorbic acid and an n-3 or n-6 essential fatty acid.

3. The method of claim 1 or 2 wherein the composition administered comprises

| | |
|---|---|
| potassium gluconate | 10 mg to 5000 mg |
| magnesium oxide | 1.0 mg to 1000 mg |
| pyridoxine hydrochloride | 0.1 mg to 500 mg |
| pantothenic acid | 0.1 mg to 1000 mg |
| ascorbic acid | 10 mg to 5000 mg |
| gamma linolenic acid | 10 mg to 5000 mg. |

4. The method of claim 3 wherein the composition administered comprises

| | |
|---|---|
| potassium gluconate | 100 mg to 1000 mg |
| magnesium oxide | 10 mg to 500 mg |
| pyridoxine hydrochloride | 5 mg to 200 mg |
| pantothenic acid | 10 mg to 500 mg |
| ascorbic acid | 100 mg to 2000 mg |
| gamma linolenic acid | 100 mg to 2600 mg. |

5. The method of claim 4 wherein the composition administered comprises

| | |
|---|---|
| potassium gluconate | 100 mg to 400 mg |
| magnesium oxide | 50 mg to 300 mg |
| pyridoxine hydrochloride | 10 mg to 100 mg |
| pantothenic acid | 50 mg to 300 mg |
| ascorbic acid | 500 mg to 1000 mg |
| gamma linolenic acid | 400 mg to 1000 mg. |

6. The method of claim 1 wherein the allergy treated is allergic asthma, urticaria, hives, eczema, psoriases, allergic conjunctivitis, or an allergic equine condition selected from obstructive pulmonary disease, laminitis and allergic eczema.

7. The method of claim 1 or 2 in which the essential fatty acid is gamma linolenic acid or dihydrogamma linolenic acid.

8. The method of claim 1 wherein the composition administered also contains at least one member selected from the group consisting of fish oil, thiamin, riboflavin, folic acid, cyanocobalamin, niacinamide, beta carotene, ergocalciferol, vitamin E, biotin, bioflavonoids, choline, inositol, boron, phosphorus, manganese, sodium, copper, iron, zinc, calcium, and selenium.

* * * * *